United States Patent
Saumarez

(10) Patent No.: US 10,265,026 B2
(45) Date of Patent: Apr. 23, 2019

(54) APPARATUS FOR RECORDING AND ANALYSING A SURFACE ELECTROCARDIOGRAM (ECG) FOR DISTINGUISHING A PHYSIOLOGICAL SIGNAL FROM NOISE

(71) Applicant: Fen EP, Ltd., Cambridge (GB)

(72) Inventor: Richard Saumarez, Cambridge (GB)

(73) Assignee: Fen EP, Ltd., Cambridge (GB)

( * ) Notice: Subject to any disclaimer, the term of this patent is extended or adjusted under 35 U.S.C. 154(b) by 0 days.

(21) Appl. No.: 15/503,665

(22) PCT Filed: Jul. 29, 2015

(86) PCT No.: PCT/GB2015/052192
§ 371 (c)(1),
(2) Date: Feb. 13, 2017

(87) PCT Pub. No.: WO2016/024082
PCT Pub. Date: Feb. 18, 2016

(65) Prior Publication Data
US 2017/0273633 A1    Sep. 28, 2017

(30) Foreign Application Priority Data

Aug. 13, 2014  (GB) .................................. 1414335.8

(51) Int. Cl.
*A61B 5/04* (2006.01)
*A61B 5/00* (2006.01)
(Continued)

(52) U.S. Cl.
CPC ............ *A61B 5/7217* (2013.01); *A61B 5/044* (2013.01); *A61B 5/04012* (2013.01); *A61B 5/0432* (2013.01); *A61B 5/0452* (2013.01); *A61B 5/04085* (2013.01); *A61B 5/4836* (2013.01); *A61N 1/025* (2013.01); *A61N 1/3625* (2013.01); *A61N 1/3702* (2013.01); *A61B 5/0464* (2013.01); *A61B 5/7203* (2013.01)

(58) Field of Classification Search
CPC . A61B 5/0468; A61B 5/04012; A61B 5/0402; A61B 5/0452
See application file for complete search history.

(56) References Cited

U.S. PATENT DOCUMENTS 7,123,954 B2 * 10/2006 Narayan ............ A61B 5/04525
600/518

FOREIGN PATENT DOCUMENTS

| WO | 9625093 | 8/1996 |
|---|---|---|
| WO | 2004026123 | 4/2004 |
| WO | 2012097067 | 7/2012 |

OTHER PUBLICATIONS

International Search Report dated Oct. 1, 2015, and received for International Application No. PCT/GB2015/052192.
(Continued)

*Primary Examiner* — George R Evanisko
(74) *Attorney, Agent, or Firm* — Fleit Gibbons Gutman Bongini Bianco PL; Jose Gutman

(57) ABSTRACT

There is described a technique using apparatus for recording and analyzing a surface electrocardiogram (ECG) for distinguishing a physiological signal from noise. The technique involves aligning and averaging multiple surface electrogram records taken for repeated pacing sequence with the same interval between pacing stimuli.

16 Claims, 19 Drawing Sheets

(51) Int. Cl.
*A61B 5/0408* (2006.01)
*A61B 5/0452* (2006.01)
*A61N 1/37* (2006.01)
*A61N 1/362* (2006.01)
*A61B 5/0432* (2006.01)
*A61B 5/044* (2006.01)
*A61N 1/02* (2006.01)
*A61B 5/0464* (2006.01)

(56) References Cited

OTHER PUBLICATIONS

Written Opinion of the International Search Authority dated Oct. 1, 2015, and received for International Application No. PCT/GB2015/052192.

* cited by examiner

Figure 10
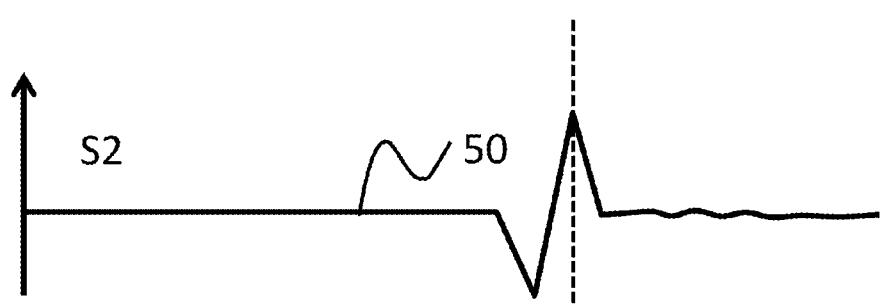
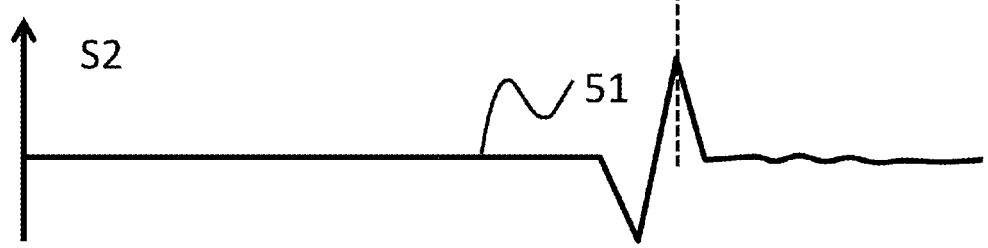

APPARATUS FOR RECORDING AND ANALYSING A SURFACE ELECTROCARDIOGRAM (ECG) FOR DISTINGUISHING A PHYSIOLOGICAL SIGNAL FROM NOISE

CROSS-REFERENCE TO RELATED APPLICATIONS

This application is based upon and claims priority to PCT Patent Application No. PCT/GB2015/052192 filed on 29 Jul. 2015, which is based upon and claims priority to GB Patent Application No. 1414335.8 filed on 13 Aug. 2014, the collective disclosure of which being hereby incorporated by reference in its entirety.

BACKGROUND

Previous research has shown that the risk of sudden death due to cardiac arrhythmias can be predicted by observing the shape of recorded endocardial electrograms in response to pacing.

The diagnostic change in electrograms consists of small deflections in the recorded electrogram following early stimulation of the heart. The heart is stimulated with apparatus that generates a stimulation sequence at one site in the heart and records electrograms from other sites within the heart.

The above technique has been used to form intra-ventricular conduction curves in which the delay of each potential within an electrogram following an early stimulation of the heart is plotted against the interval between the stimulus and the last stimulus of a constant rate sequence of stimuli. Typically this involves between 230 and 250 early stimuli with the interval at which each early stimulus is applied is reduced by one millisecond on each occasion. These curves have characteristic shapes that can be analyzed to estimate the risk of sudden death. This technique is described in GB2439562.

In previous research using this technique, the diseases that affect the heart have been assumed to uniformly affect all of the tissue within the heart. In the case of patients that have recovered myocardial infarction, the abnormalities are confined to the tissue that surrounds the infarct. While it is possible to make detailed endocardial recordings in that region, such a technique is too complex for routine use, because for example, the need for multiple left ventricular electrodes.

A surface electrocardiogram (ECG) consists of potentials measured on the torso surface, these represent the weighted sum of all of the currents active within the hear. Surface ECGs are commonly used for diagnostic purposes.

The small deflections following an early stimulus can be detected using a surface ECG recording although the detected deflections are extremely small. Therefore a process needs to be carried out to distinguish these small deflections from noise.

A common technique is to average the signals to accentuate small potentials from the noise.

It is well known that some patients have small delayed potentials discernible in their average ECG during sinus rhythm and this has some association with the risk of sudden death.

BRIEF SUMMARY

According to a first aspect of the invention there is provided apparatus for recording and analyzing a surface electrocardiogram (ECG) for distinguishing a physiological signal from noise; the apparatus comprising:

a) means to pace the heart in a pacing sequence comprising a number of stimuli with a constant interval followed by an early stimulus, in which the interval between the early stimulus and the preceding constant rate stimulus is smaller than the interval between the constant rate stimuli;

b) means to repeat the pacing sequence multiple times with the same interval between the early stimulus and the preceding constant rate stimulus;

c) means to repeat the pacing sequence multiple times with a different interval between the early stimulus and the preceding constant rate stimulus;

d) means to create surface electrocardiogram records during the repeated pacing sequences in b) and c);

e) means to average the surface electrocardiogram records corresponding to each of the early stimuli paced in b); and f) means to average the surface electrocardiogram records corresponding to each of the early stimuli paced in c).

The apparatus thereby provides the ability to determine changes in intraventricular conduction thereby building a conduction curve that is analogous to that obtained using endocardial measurements.

In a preferred embodiment, the apparatus comprises means to compare the averaged recorded surface electrocardiograms taken from e) and f) and to display the differences thereby displaying a conduction curve.

A surface electrocardiogram shows physiological variability in its shape as a consequence of respiration, blood pressure control cycles etc. In order to compensate for this, it is preferred that there is at least one sensing endocardial cardiac electrode and means for using a signal sensed by the at least one sensing endocardial cardiac electrode to compensate for delays and/or distortion of the surface electrocardiogram.

Preferably the at least one sensing endocardial cardiac electrode is used to derive an interval between the pacing stimulus provided by a pacing electrode and the onset of activation of myocardium in a region proximate to the pacing electrode. The variation in this interval represents stimulus to tissue latency and its measure allows alignment of the surface electrocardiogram signals to a common timing reference. Thus it is also preferred that the interval derived for each stimulus is used to align the surface ECG record corresponding to that stimulus to a common time reference.

By aligning of the surface ECG signals improved resolution of its features will be obtained following averaging as misaligned signals will tend to degrade detection of small potentials.

So that the conduction time between electrodes will be short as compared to the stimulus to tissue latency, it is preferred that the distance between the pacing electrode and the at least one sensing endocardial cardiac electrode is substantially 1 cm or less.

It is further preferable that the apparatus comprises a first sensing cardiac electrode that is proximate to a pacing electrode and a second sensing cardiac electrode that is remote to the pacing electrode.

It is preferred that the pacing electrode, first sensing cardiac electrode, and where applicable second sensing cardiac electrode are located within the right ventricle of the heart. Thereby avoiding additional complexity of left ventricular catheterisation.

The apparatus may also comprise means to determine an interval between a signal from the first sensing electrode resulting from the activation of myocardial tissue proximate the first electrode and a second signal from the second sensing electrode resulting from activation of myocardial tissue proximate the second electrode. This interval represents conduction velocity throughout the heart and may be used to time stretch or time compress the surface electrocardiogram records so that each record is the same length. This has the effect also of increasing resolution of the averaged surface ECG signal as a result of better alignment of the potentials when averaging takes place.

The interval between potentials as sensed by the proximate electrode and remote electrode is measured, preferably by cross correlation. (Variations in the interval may be caused by physiological effects such as respirations, fluctuations in blood pressure etc.) This allows stretching of the individual surface ECG records for each response to the early stimuli so as to become of equal length.

The timings of pacing stimuli are derived from a clock with a frequency of 1 KHz resulting in 1 ms time resolution. This frequency may result in stimuli that are coherent with mains frequency interference and its harmonics. Therefore the noise in the surface ECG may not be truly random and so not eliminated by averaging. To overcome this, it is preferred that a pseudo-random time jitter is introduced into the constant rate stimuli. More preferably the pseudo-random time jitter is introduced into the first constant rate stimulus of each pacing sequence. This will decouple the pacing sequence from AC noise.

A first assumption behind averaging is that each physiological signal being averaged is identical. A second assumption is that the measurements reflect a pure electrophysiological process, however, where there is progressive cardiac ischemia conduction within the heart with be affected as the pacing proceeds that will alter the morphology of the surface ECG and in particular the responses associated with the constant rate stimuli.

In order to identify progressive changes in shape of the response to constant rate stimuli, it is preferred that each ECG record is divided into sub records and the change in signal power (the square of the signal amplitude) is determined each a new record added to the average record. If the signal power fails to decline as new records are added it will indicate progressive change in the ECG morphology and non stationarity of the averaging process which is indicative of ischemia.

BRIEF DESCRIPTION OF THE DRAWINGS

The accompanying figures in which like reference numerals refer to identical or functionally similar elements throughout the separate views, and which together with the detailed description below are incorporated in and form part of the specification, serve to further illustrate various embodiments and to explain various principles and advantages all in accordance with the present disclosure, in which:

FIG. 10 is a schematic illustrating misalignment between successive potentials following an extra stimulus;

DETAILED DESCRIPTION

As required, detailed embodiments are disclosed herein; however, it is to be understood that the disclosed embodiments are merely examples and that the devices, systems and methods described herein can be embodied in various forms. Therefore, specific structural and functional details disclosed herein are not to be interpreted as limiting, but merely as a basis for the claims and as a representative basis for teaching one of ordinary skill in the art to variously employ the disclosed subject matter in virtually any appropriately detailed structure and function. Further, the terms and phrases used herein are not intended to be limiting, but rather, to provide an understandable description. Additionally, unless otherwise specifically expressed or clearly understood from the context of use, a term as used herein describes the singular and/or the plural of that term.

The terms "a" or "an", as used herein, are defined as one or more than one. The term "plurality", as used herein, is defined as two or more than two. The term "another", as used herein, is defined as at least a second or more. The terms "including" and "having," as used herein, are defined as comprising i.e., open language. The term "coupled," as used herein, is defined as "connected," although not necessarily directly, and not necessarily mechanically. "Communicatively coupled" refers to coupling of components such that these components are able to communicate with one another through, for example, wired, wireless or other communications media. The term "communicatively coupled" or "communicatively coupling" includes, but is not limited to, communicating electronic control signals by which one element may direct or control another. The term "configured to" describes hardware, software or a combination of hardware and software that is adapted to, set up, arranged, commanded, altered, modified, built, composed, constructed, designed, or that has any combination of these characteristics to carry out a given function. The term "adapted to" describes hardware, software or a combination of hardware and software that is capable of, able to accommodate, to make, or that is suitable to carry out a given function.

Figure 1:
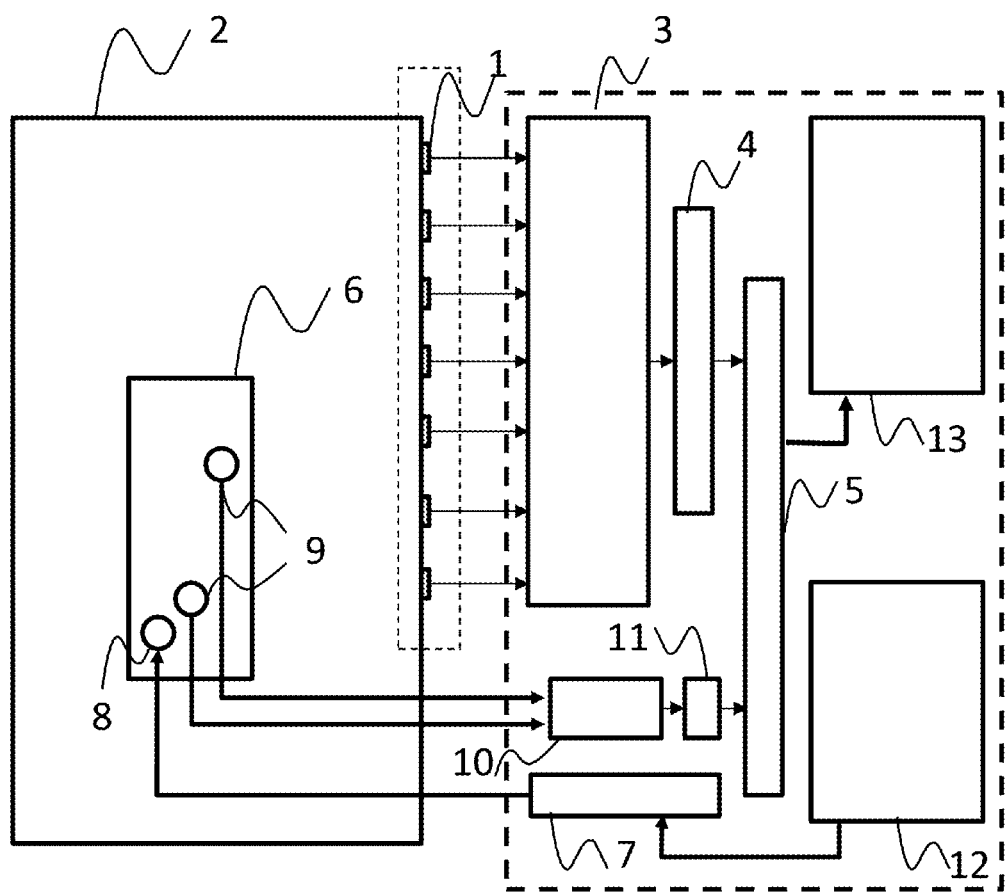
FIG. 1 is a schematic of apparatus to stimulate a heart, make a surface ECG, and subsequently analyze the resulting data.
Figure 2:
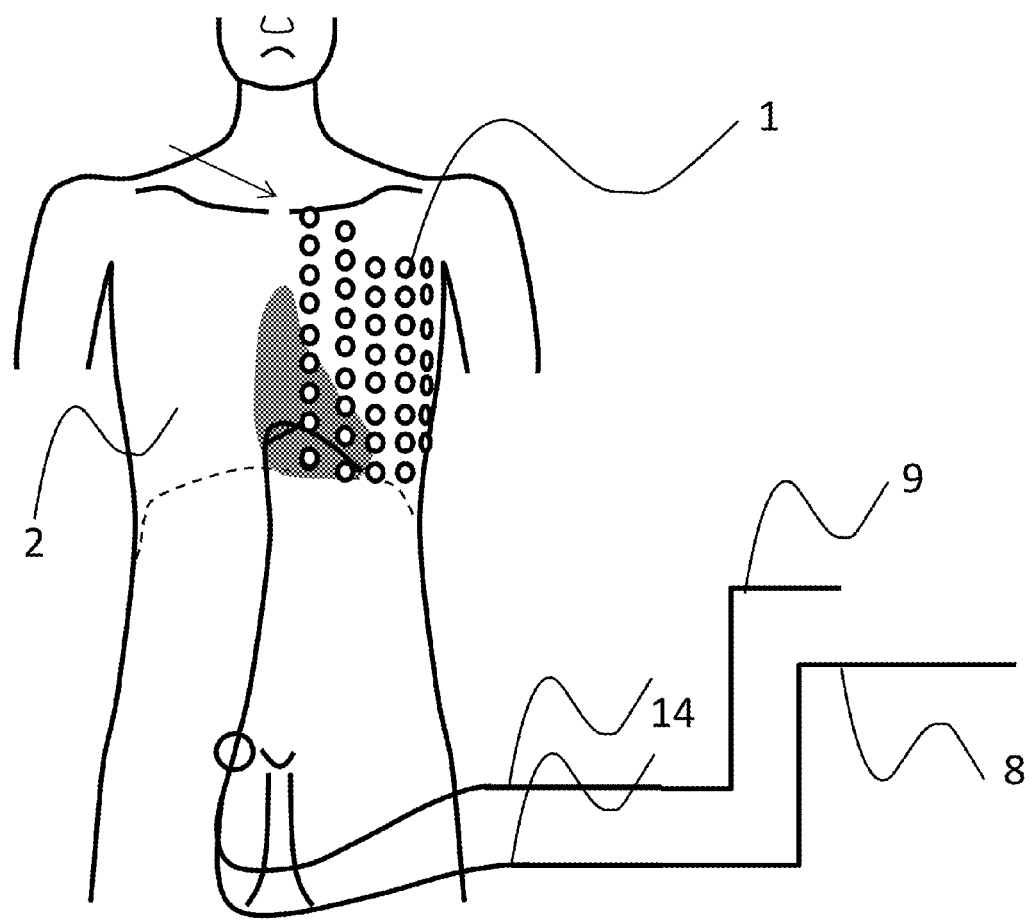
FIG. 2 is a schematic illustrating the electrodes used to pace the heart and take recording from within the heart and from the torso surface.
Figure 3:
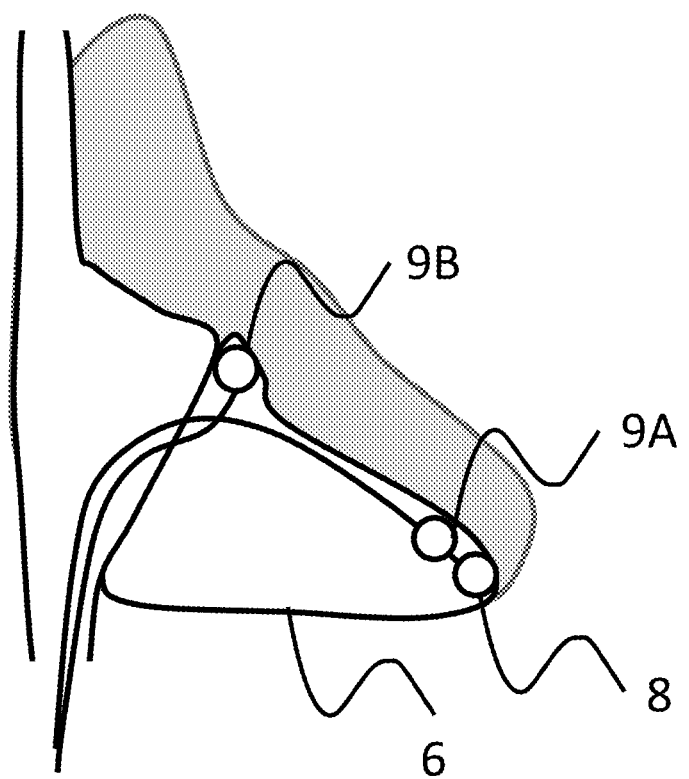
FIG. 3 is an antero-posterior projection of the hearts showing the relative positions of the pacing electrode and sensing electrodes.

With reference to FIG. 1 there is shown apparatus comprising a recording, pacing and an analysis system. The system comprises an array of thoracic surface electrodes 1 that sense potentials from torso surface 2, illustrated in FIG. 2. The sensed potentials are amplified by a multichannel amplifier system 3 and digitized with an analogue to digital converter 4 and the digital signals stored in a memory 5. The heart 6 is stimulated with a pacing system 7 having an electrode 8 placed within the heart. Further electrodes 9 placed at alternative positions within the heart, as shown in FIG. 3 sense potentials from within the heart 6. The endocardial electrodes 8, 9 are inserted via catheters 14 into the right ventricle. The potentials sensed by electrodes 9 are amplified by amplifier 10, digitized by an ADC 11 and stored in memory 5. The stimulation of the heart and recording of the sensed potentials are controlled by a computer program 12. Following a recording process, the recorded data in memory 5 is analyzed by a further program 13.

FIG. 3 shows the pacing electrode 8 positioned at a tip of a catheter 15A used to stimulate the heart 6 and a second electrode 9A mounted on the same catheter 15A within 1 cm of the pacing electrode 8 for recording a response. A second recording electrode 9B on a second catheter 15B is positioned in the right ventricle of the heart 6 as far as possible from the pacing electrode 8. In addition to pacing electrode 8 a further pacing electrode (not shown) can be used to stimulate the high right atrium to avoid fusion beats.

Figure 4:
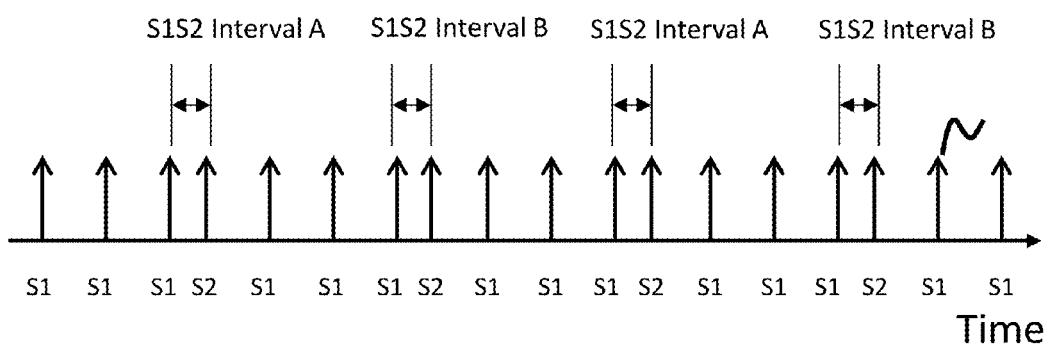
FIG. 4 is a schematic of the stimulation sequence used to pace the heart.

The heart 6 is paced with a pacing sequence comprising a number of constant rate stimuli (S1) followed by an extra stimulus S2. The S1-S2 interval is smaller than the S1-S1 interval. FIG. 4 illustrates four of these sequences showing in this instance two S1-S2 intervals in the sequences S1-S2A, S1-S2B, S1-S2A, S1-S2B, . . . . Alternatively the sequence may be delivered as S1-S2A, S1-S2A, . . . S1-S2B, S1-S2B, . . . FIG. 4 shows these sequences repeated twice but in practice it is preferred that they are repeated several hundred times. The number of repeats may be determined by the convergence of the signal.

Although only two intervals are shown, in practice eight intervals used to achieve a study in a practical length of time. However, more intervals may be used where time allows.

Figure 5:
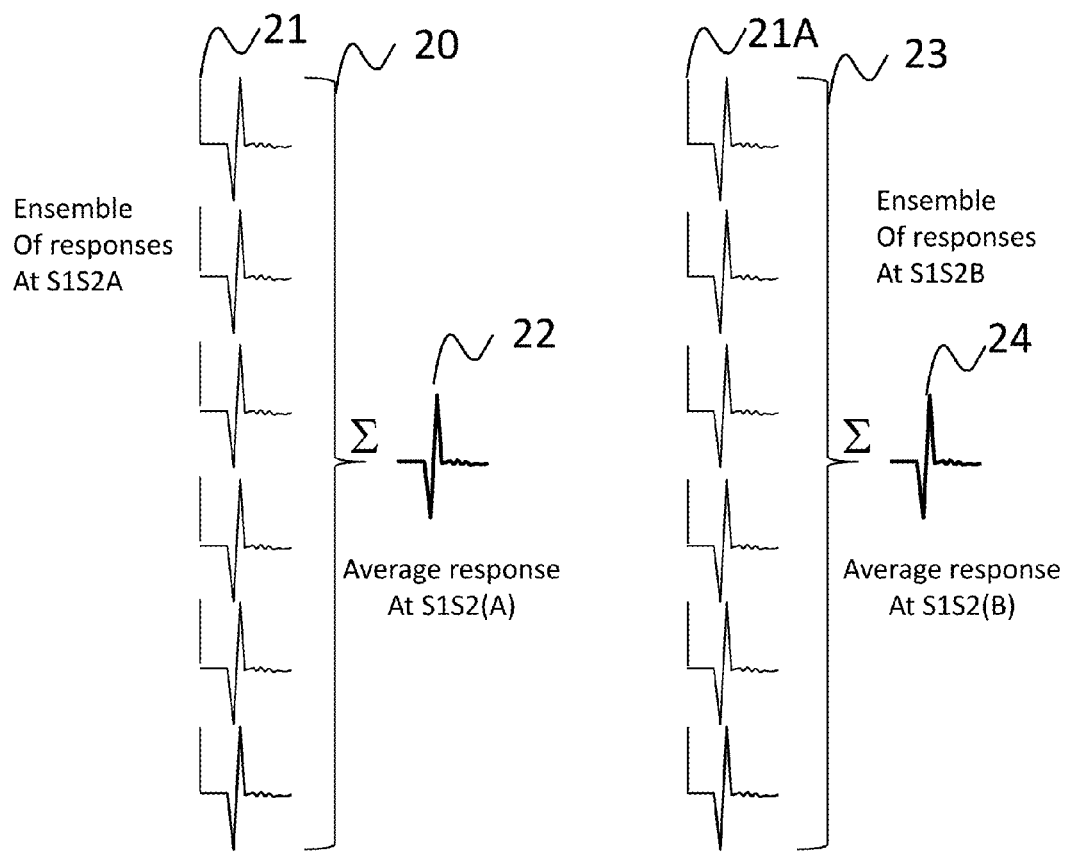
FIG. 5 is a schematic indicating alignment of surface ECG responses for different coupling intervals being averaged.

FIG. 5 illustrates the process of averaging each recorded signal in response to S2 stimuli following the same S1-S2 interval; in this case the intervals A and B as shown in FIG. 4.

Each recorded signal of interval A 20 are aligned in time using the pacing stimulus 21 within the recording. The aligned recorded signals are then summed to form an average signal 22 of interval A. The same process is also performed on each recorded signal 23 of interval B to create an average recorded signal of interval B 24. The averaging process reduces the noise by the square root of the number of averages for a Gaussian noise. It is also known that the averaging process acts as a low-pass filter that acts selectively on the noise.

Figure 6:
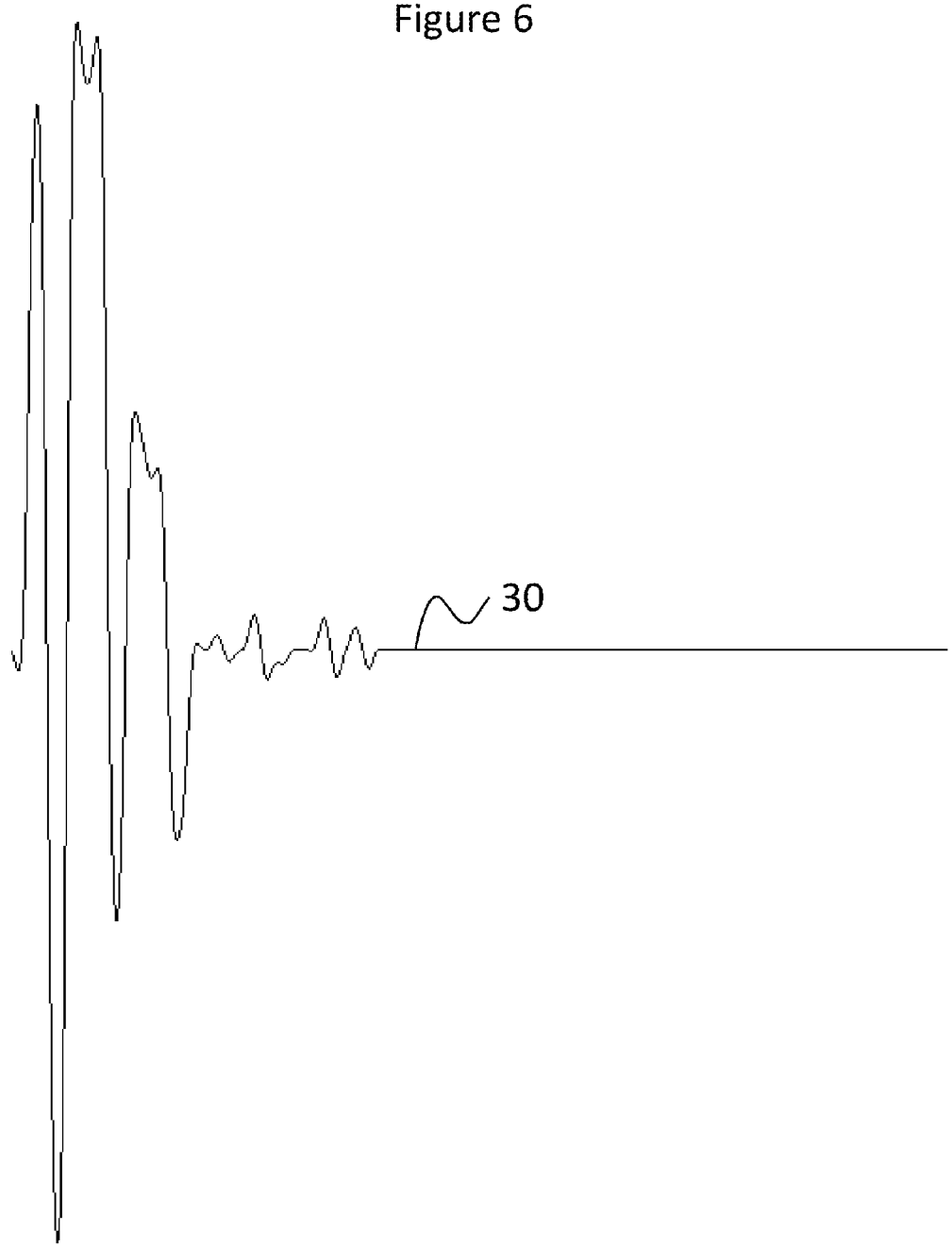
FIG. 6 is a simulated high-pass filtered surface electrocardiogram signal.
Figure 7:
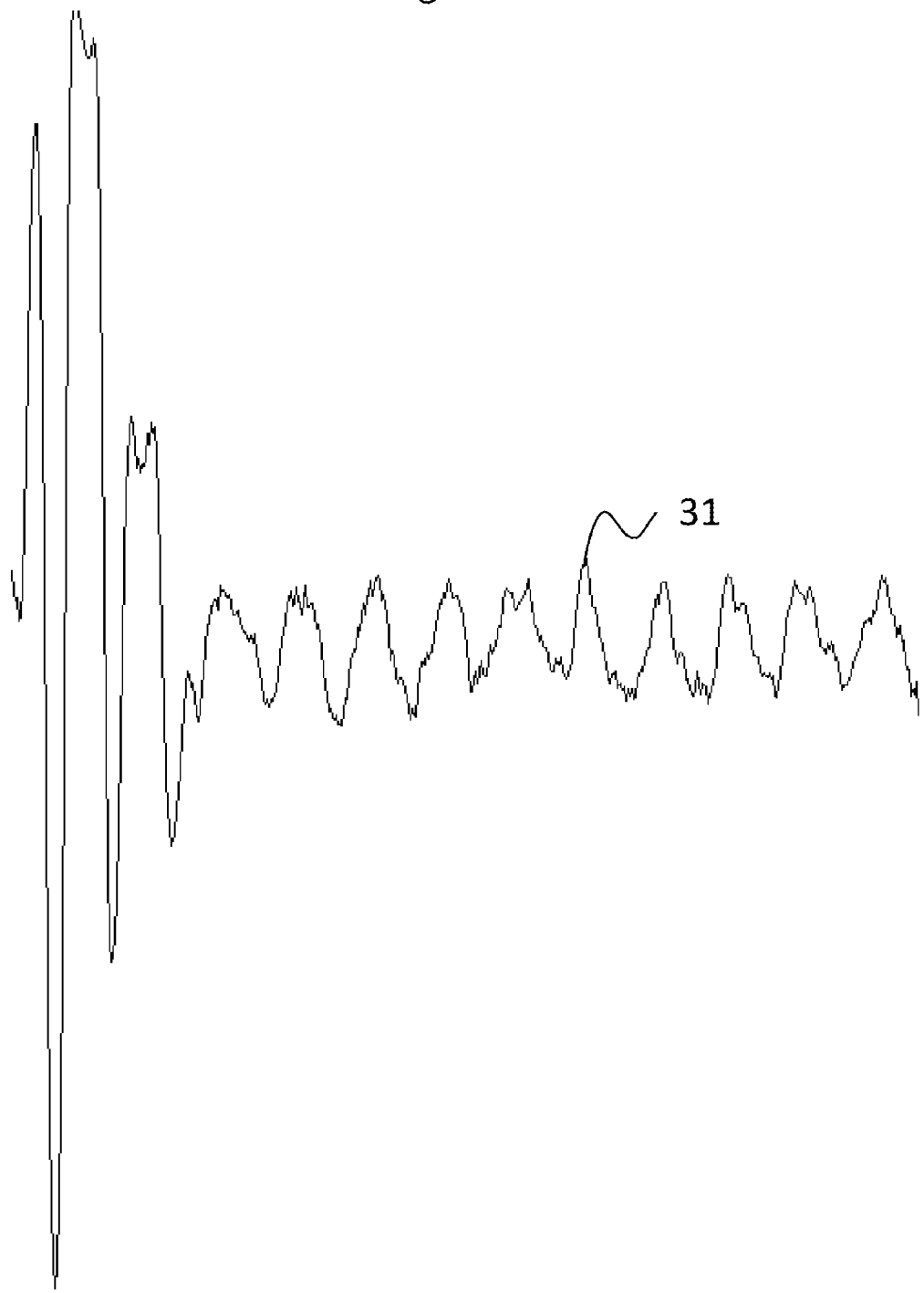
FIG. 7 is the surface ECG signal of FIG. 6 with added noise.
Figure 8:
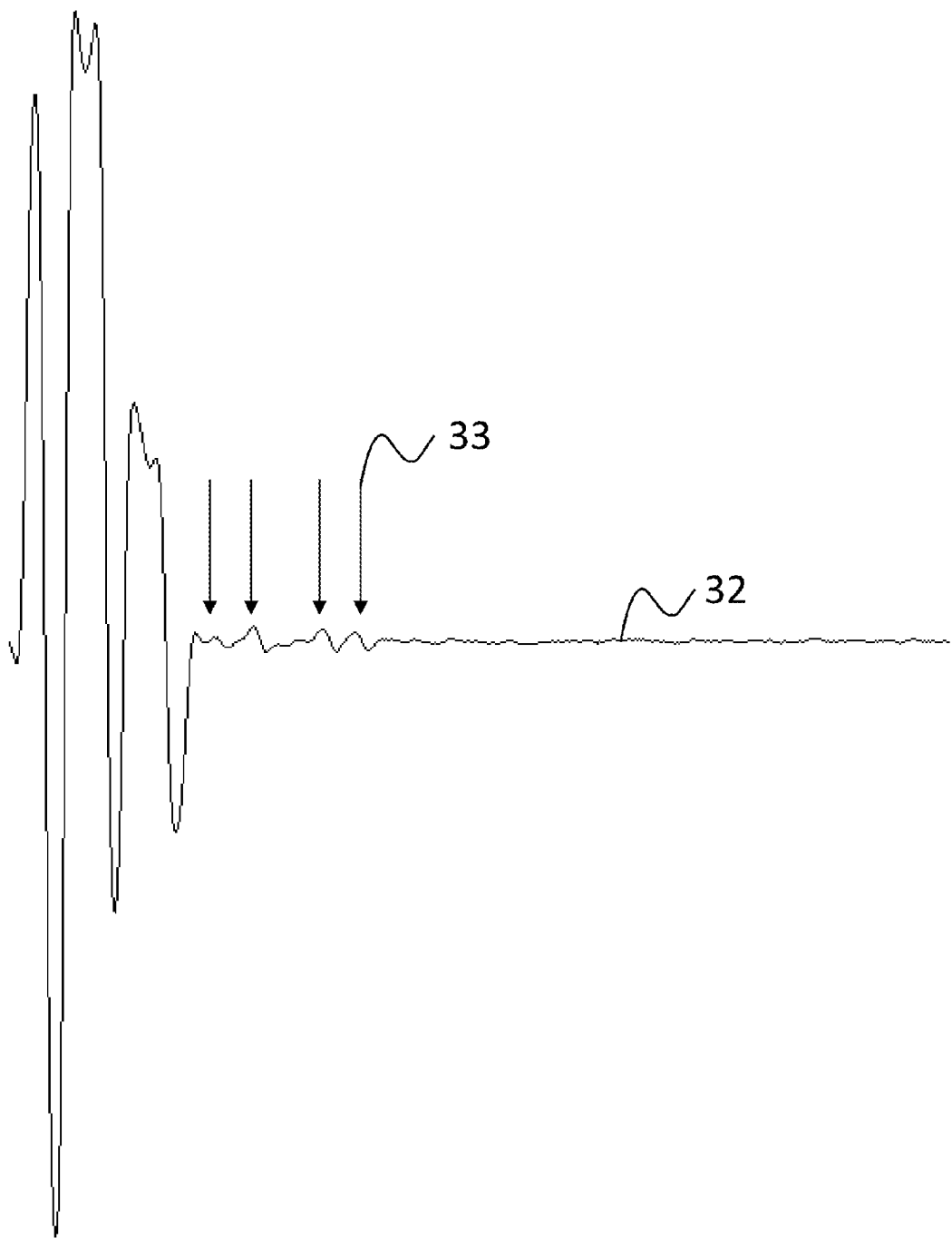
FIG. 8 is an averaged ECG signal (similar to FIG. 7) illustrating the cancelling out of noise.

FIGS. 6, 7 and 8 illustrate an ideal process showing a simulated high-pass filtered surface ECG signal 30. Two hundred records the signal shown in FIG. 6 are creates to represent records taken following S2 stimuli, pseudo-random noise is added to each record 31, one of which is shown in FIG. 7. These are then averaged to give the signal 32 shown in FIG. 8, where the small potentials 33 in the terminal portion are discernible.

In practice, this process will be degraded in a number of ways rendering small potentials indiscernible. These ways and their remedies described.

Figure 9:
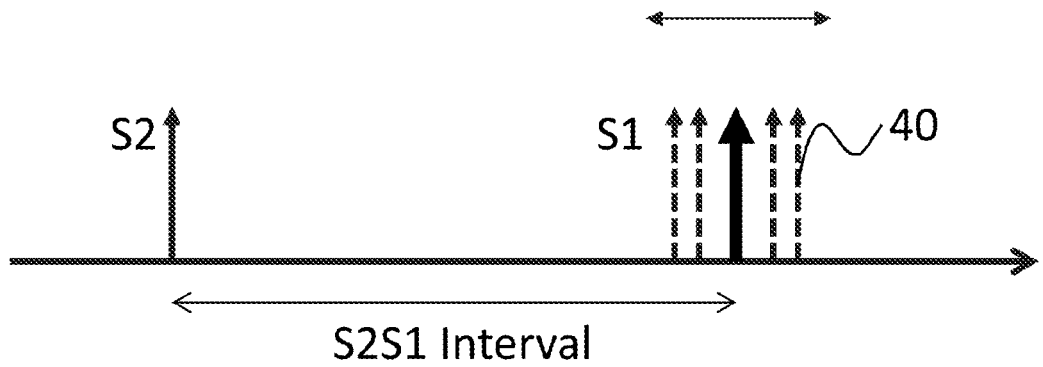
FIG. 9 is a schematic showing pseudo-random jitter in a first constant rate stimulus in a sequence.

A fundamental assumption is that that noise is unrelated to the signal being detected. Conventionally stimuli are calculated in 1 ms intervals and are timed using a 1 KHz clock. This may create synchronization of the pacing process with mains AC noise or its harmonics. This is overcome, as illustrated in FIG. 9 by imposing a pseudo-random jitter 40 in the interval between the S2 stimulus and S1 stimulus following it. The subsequent stimuli in the sequence following the S1 stimulus maintain the same interval from each other such that in effect all the stimuli within a sequence are jittered by the same amount. This will decouple the pacing sequence from periodic signals in the noise.

Another problem is that signals following a S2 stimulus may be misaligned as a consequence of physiological processes such as respiration. FIG. 10 shows the misalignment of potentials between two recorded signals 50, 51 by an interval 52 caused by said physiological processes.

This misalignment results in small potentials being not added together and so will not be detected in the averaged signal 32.

Figure 11:
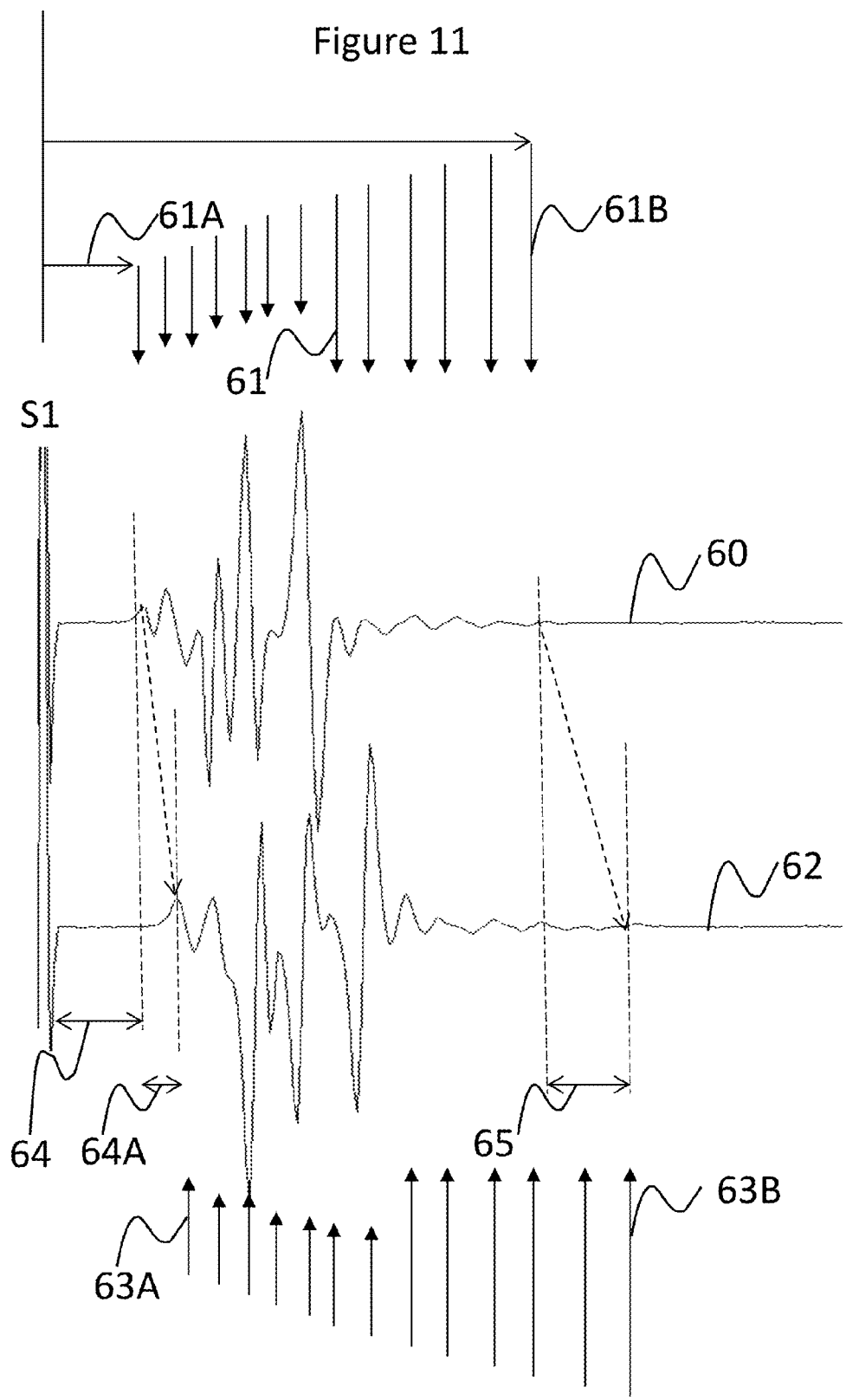
FIG. 11 illustrate recorded endocardial electrograms following a constant rate stimulus.

FIG. 11 shows two intracardiac electrograms 60 62 recorded by remote electrode 9B following an S1 stimulus. The electrograms 60 62 have been aligned using the S1 stimulus as the reference point. Notwithstanding this alignment, it can seen that there remains miss-alignment between the significant potentials 61 63 of the signals 60 62.

The first potential 61A in signal 60 following a S1 stimulus precedes the first potential 63A in signal 62. This distance 64 between the first potentials 61A 63A and S1 stimulus represents the signal to tissue latency. The difference in time between the first potentials 61A 63A from the S1 stimulus the represents variation in signal to tissue latency 64A.

Similarly the potential 61B in signal 60 precedes the equivalent potential 63B in signal 62 by a greater interval 65 than the stimulus to tissue latency indicating time dilation of signal 62 with respect to signal 60.

Figure 12:
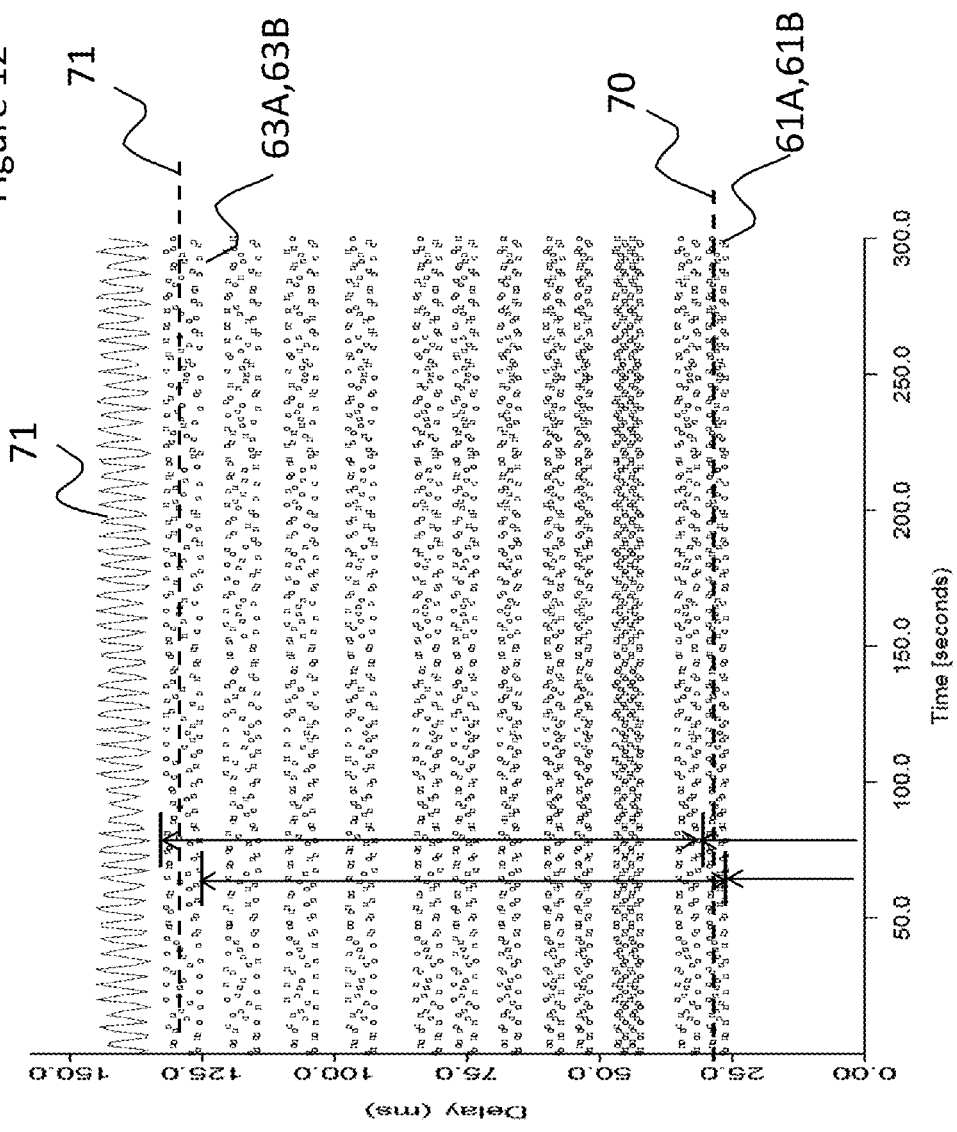
FIG. 12 is a plot showing delays of endocardial potentials following successive constant rate stimuli.

FIG. 12 shows the delays 61 and 63 measured for successive S1 stimuli and each potential 61 63 is plotted as the ordinate against the time at which the stimulus occurred. The mean interval between the S1 stimulus and the first potentials 61A 63A are shown by line 70. Similarly the mean interval between the S1 stimulus and the potentials 61B is shown by line 71. This variation will degrade detection of potentials of short duration.

Line 72 is an interpolated version of data points 61A 61B. It has a periodicity of approximately 11.5 per minute that likely to be due to respiration. The degree of variation in stimulus to tissue latency and time dilation of the electrogram are comparable to the width the small potentials that one would wish to detect in the electrocardiogram and therefore this degree of signal variation is likely to degrade the results of signal averaging. It should be noted this effect is highly variable between patients.

This problem can be minimized by using intracardiac reference electrograms.

Figure 13:
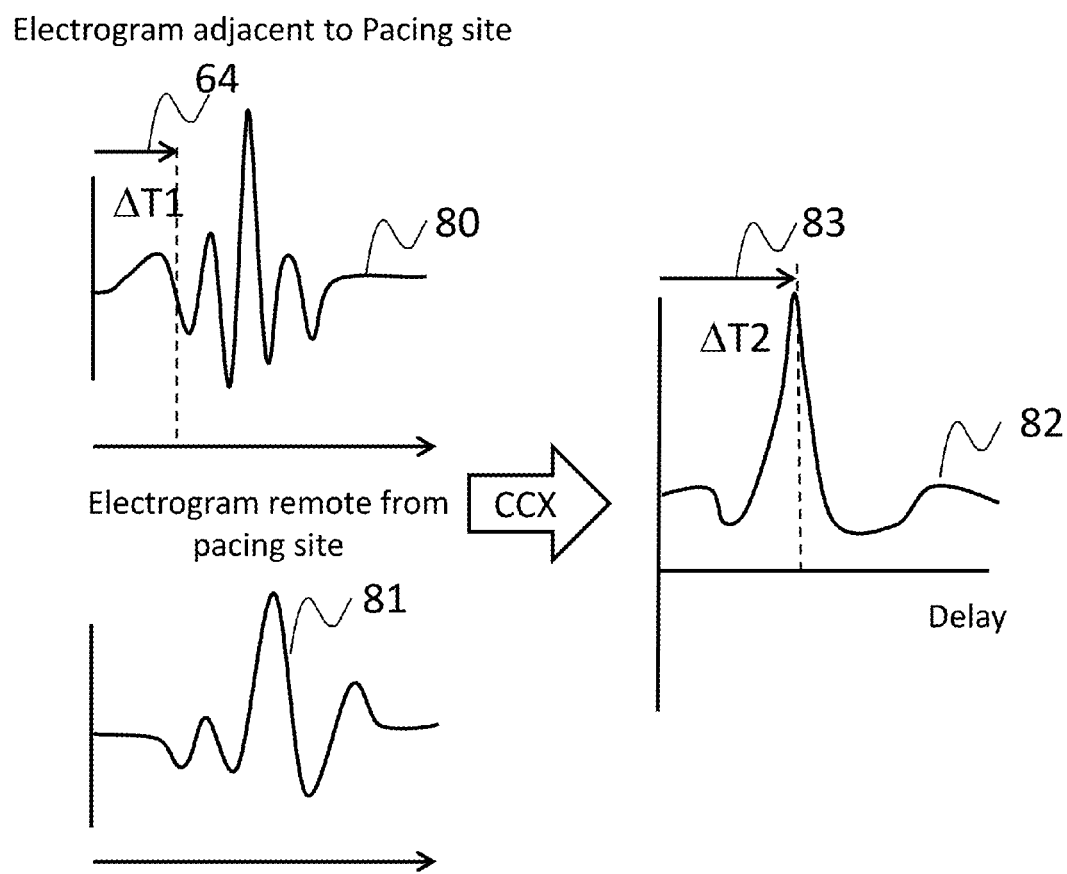
FIG. 13 illustrates the process of cross correlating signals from proximate and remote recording electrodes to derive the delay between them.

FIG. 13 illustrates electrograms 80 81 taken from the proximate and remote sensing electrodes 9A 9B respectively. The stimulus to tissue latency 64 marked ΔT1 is determined from the proximate electrode signal 80. The two electrograms 80 81 are cross-correlated to give the cross-correlation function 82 showing a peak when the two are most correlated. The delay 83 of this peak ΔT2 gives the delay between the electrograms 80 81. The mean delay of ΔT2 for all records at a particular S1-S2 interval is determined.

Provided that ΔT2 for an individual record is close to the mean ΔT2 of all records, it indicates that there has been no significant stretch in the individual record, and any misalignment is therefore due to stimulus to tissue latency.

Figure 14:
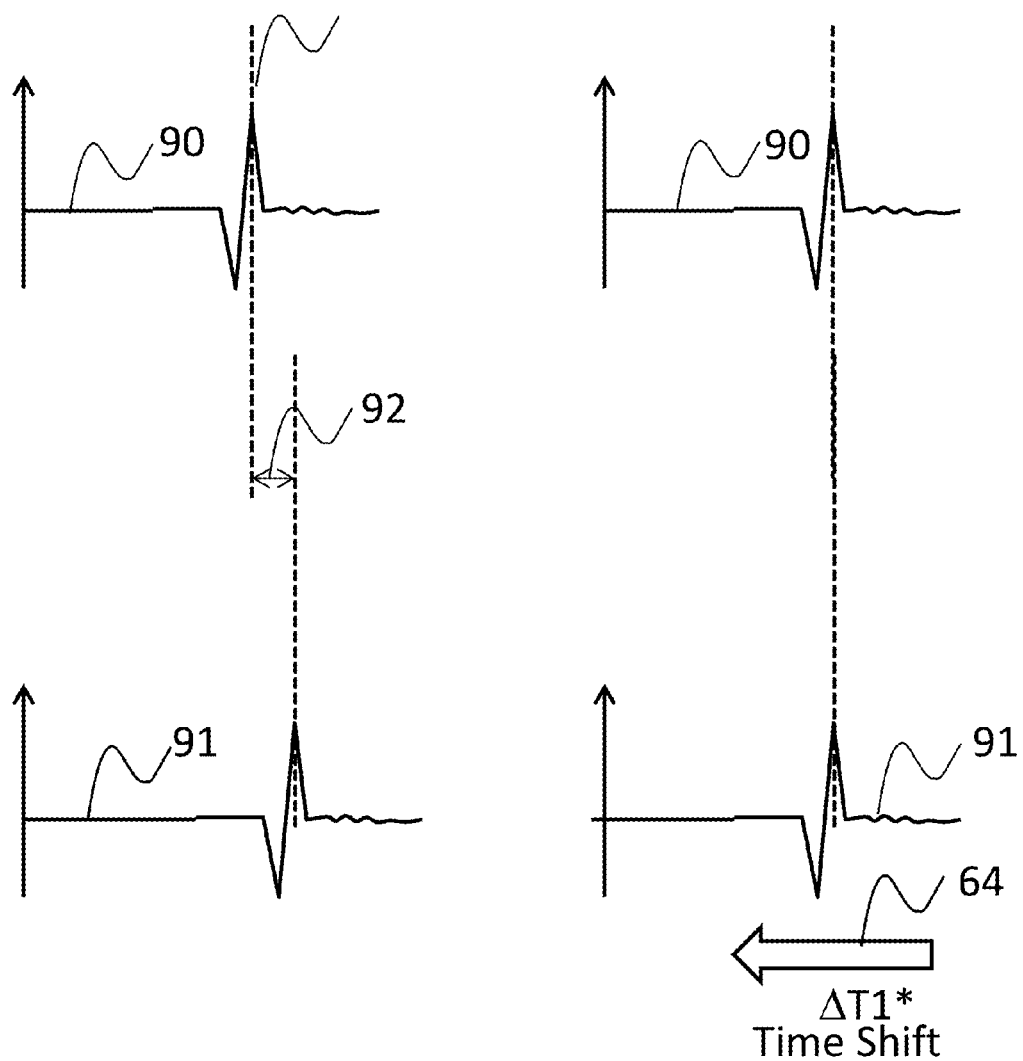
FIG. 14 shows alignment of two signals using stimulus to tissue latency.

FIG. 14 shows two misaligned signals 90 91 from a surface ECG. The misalignments shown as 92 are due to stimulus to tissue latency. The signal 91 is shifted by the difference in stimulus to tissue latency from the mean, ΔT1*64 derived using the endocardial electrograms so that it aligns with the signal 90.

Figure 15:
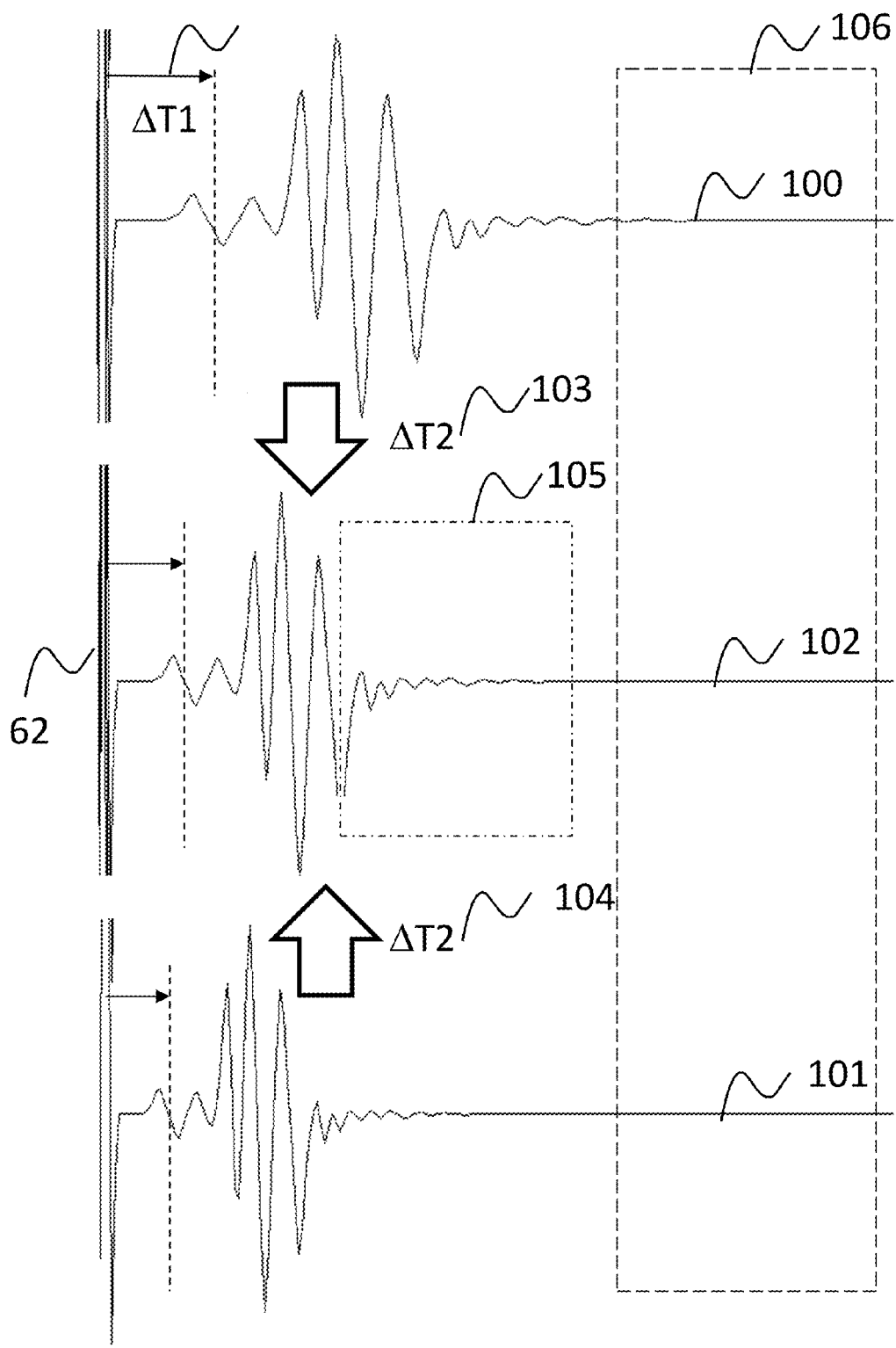
FIG. 15 illustrates time compression and time dilation of electrograms to give a consistent length signal.

FIG. 15 shows two surface ECG records 100 101 in response to the same interstimulus interval, showing different stimulus to tissue latency and time dilation A further signal 102 shows mean stimulus to tissue latency and time dilation. After correction of signals 100 101 for the stimulus to tissue latency, thereby aligning their first potential with that of record 102, record 100 is compressed according to the interval ΔT2 103 derived for that record 100 and record 101 stretched using ΔT2 104 derived for that record, so that both records 100 1001 have a ΔT2 that corresponds to the mean ΔT2 for record 102. The stretching and compression is achieved by frequency domain interpolation and resampling on a constant time interval.

A portion 105 of each signal is believed to contain small physiologically derived signals and a later portion 106 is assumed to contain only noise.

We measure the sum of the power in the signals in the physiological region 105 and the noise region 106.

In practice stretching and compression may by assuming that the degree of requirement of length change of an individual signal is a function of ΔT2 that may be described by a few parameters, thereby allowing some degree of non-linearity in the stretching.

An objective function is defined which is the power in the assumed portion of the averaged signals following time stretching/compression divided by the power considered to be noise that is similarly stretched/compressed. Therefore the parameters of the stretching/compressing process may be determined by maximizing this function using conventional numerical methods.

During a protracted pacing run myocardial ischemia may be provoked. It is known that that ischemia causes increased conduction delays and local block leading to lengthening and additional potentials in local endocardial electrograms which may be reflected in the surface ECG. This may be detected by identifying non-stationarity in the responses to S1 stimuli that should remain constant.

Figure 16:
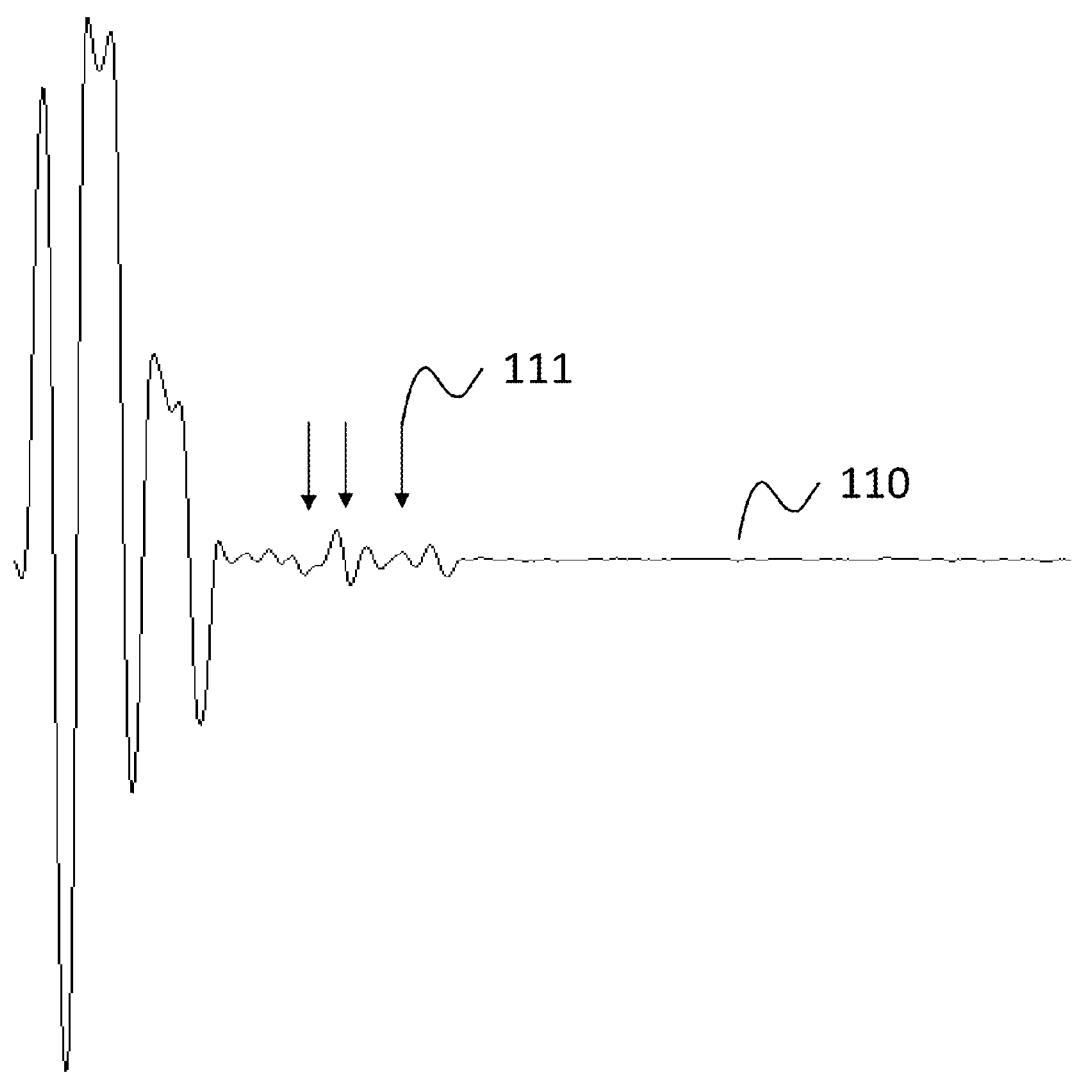
FIG. 16 show the results of averaging a non-stationary signal.

FIG. 16 show a stimulated averaged signal derived from signals in response to an S1 stimulus having non-stationary potentials assumed to be caused from ischemia.

Figure 17:
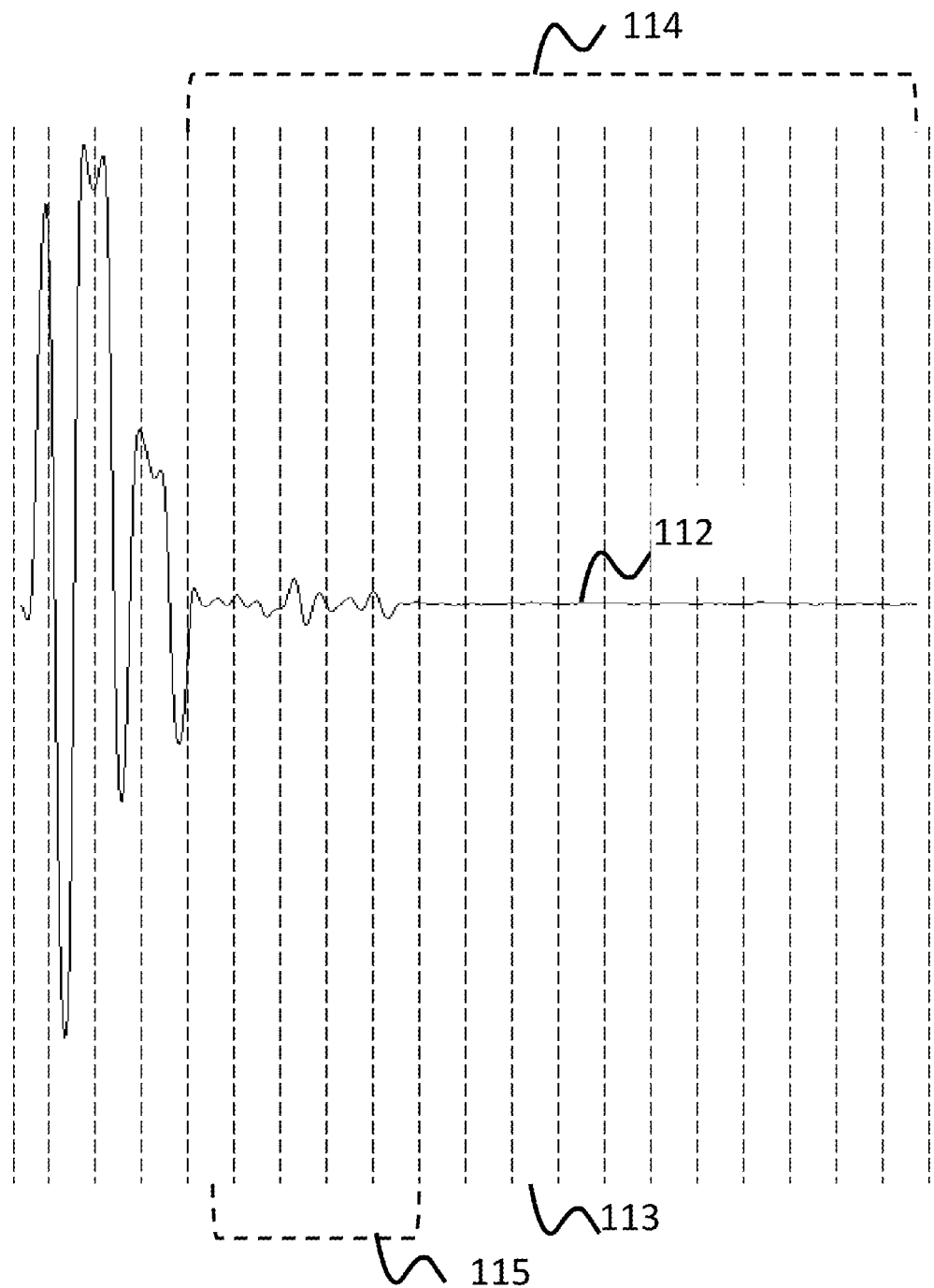
FIG. 17 shows the segmentation of a signal into successive sub-records.

The effects of non-stationarity can be detected by segmenting each individual record 112 into sub-records 113 as shown in FIG. 17. The average signal power (squared amplitude) in each sub record is calculated.

Figure 18:
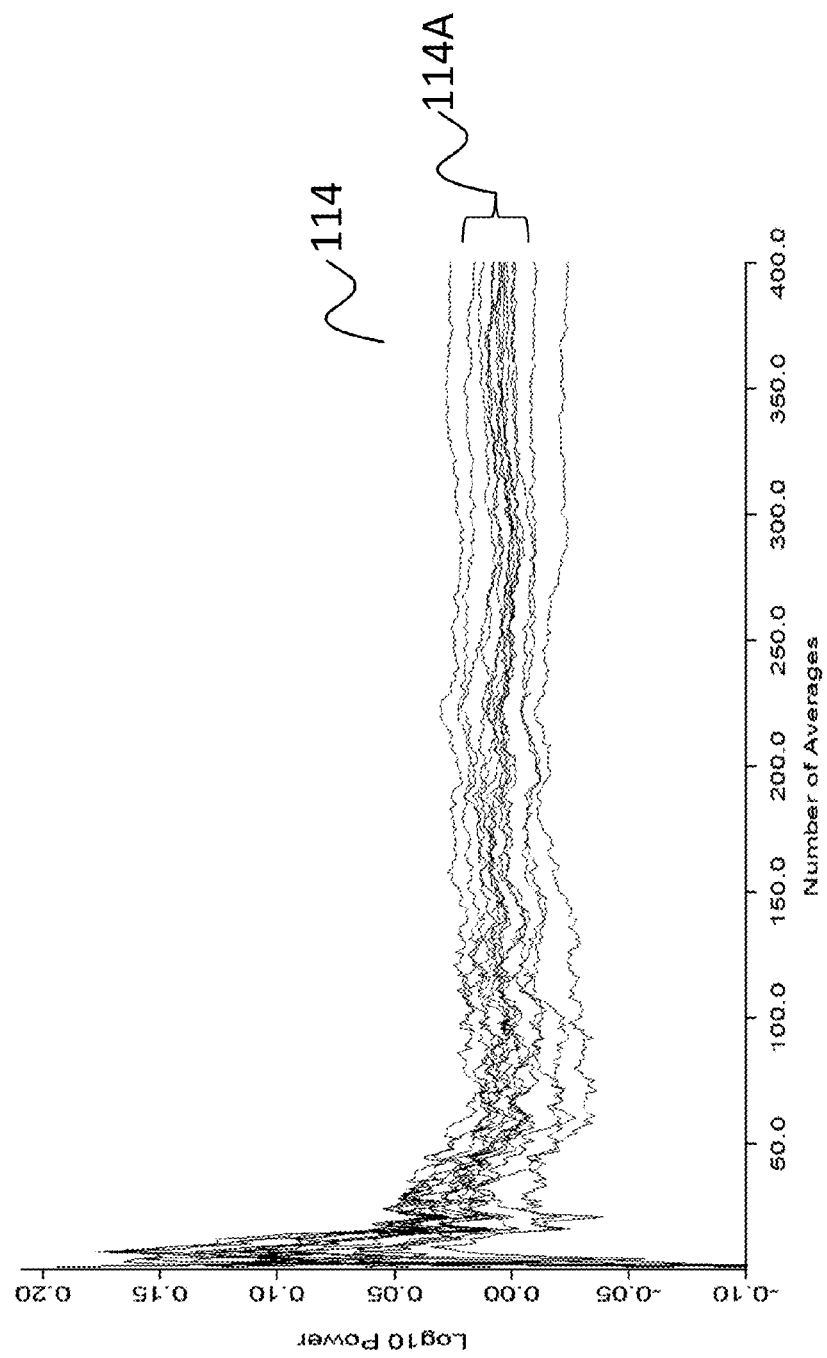
FIG. 18 shows the power in selected sub records varying as the number of averages increases for a stationary signal.

FIG. 18 shows the logarithm of the power in each sub record 114 for a stationary signal as each record added to the average record. After roughly two hundred records have been averaged, the power in each sub record approaches a stable value 114A.

Figure 19:
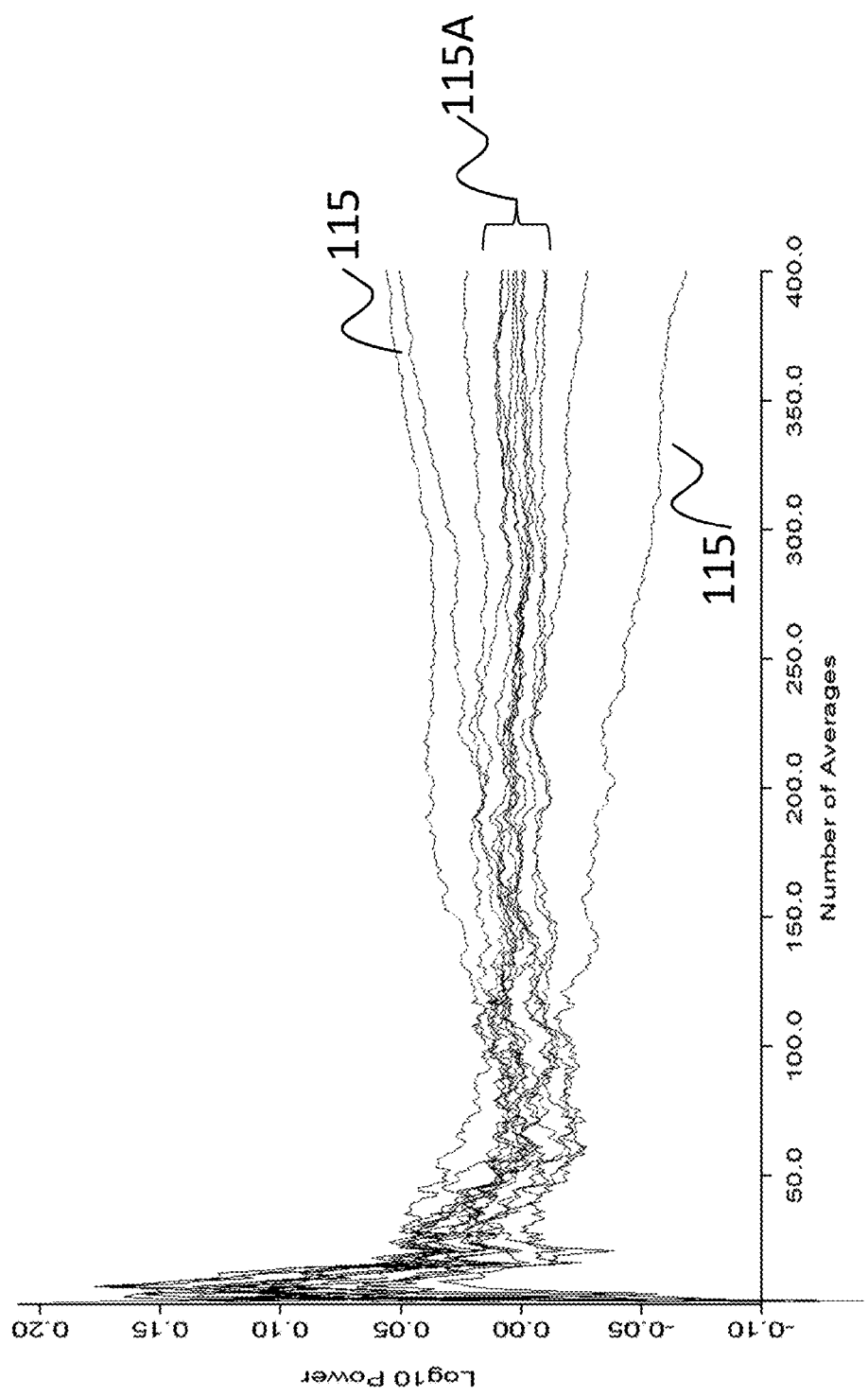
FIG. 19 a similar plot to FIG. 18 for the non-stationary signal illustrated in FIG. 17.

FIG. 19 shows the results for a non stationary signal assumed to be caused by ischemia. The sub records 115 close to the end of the assumed physiological portion of the signal deviate with increasing number of averages as potentials in that sub record increase or diminish. The final sub records 115A that are assumed to be noise only do not change.

The Abstract is provided with the understanding that it is not intended be used to interpret or limit the scope or meaning of the claims. In addition, in the foregoing Detailed Description, various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

The corresponding structures, materials, acts, and equivalents of all means or step plus function elements in the claims below are intended to include any structure, material, or act for performing the function in combination with other claimed elements as specifically claimed. The description herein has been presented for purposes of illustration and description, but is not intended to be exhaustive or limited to the examples in the form disclosed. Many modifications and variations will be apparent to those of ordinary skill in the art without departing from the scope of the examples presented or claimed. The disclosed embodiments were chosen and described in order to explain the principles of the embodiments and the practical application, and to enable others of ordinary skill in the art to understand the various embodiments with various modifications as are suited to the particular use contemplated. It is intended that the appended claims below cover any and all such applications, modifications, and variations within the scope of the embodiments.

Although specific embodiments of the subject matter have been disclosed, those having ordinary skill in the art will understand that changes can be made to the specific embodiments without departing from the scope of the disclosed subject matter. The scope of the disclosure is not to be restricted, therefore, to the specific embodiments, and it is intended that the appended claims cover any and all such applications, modifications, and embodiments within the scope of the present disclosure.

The invention claimed is:

1. Apparatus for analyzing a surface electrocardiogram (ECG) for distinguishing a physiological signal from noise, comprising:
   at least one sensing cardiac electrode for insertion into a heart of a patient;
   a pacing electrode for insertion into a heart of a patient;
   an array of surface thoracic electrodes for placement on a torso of the patient; and
   a recording, pacing and analysis system coupled to the at least one sensing cardiac electrode, the pacing electrode, and the array of surface thoracic electrodes, the recording, pacing and analysis system arranged and configured to:
   a) using the pacing electrode, pace the heart in a pacing sequence comprising constant rate stimuli followed by an early stimulus, in which an interval B between the early stimulus and a preceding constant rate stimulus of the constant rate stimuli is smaller than an interval A between each stimulus of the constant rate stimuli;
   b) repeat the pacing sequence multiple times wherein each time the interval B between the early stimulus and the preceding constant rate stimulus has a same duration;

c) repeat the pacing sequence multiple times wherein each time the interval B between the early stimulus and the preceding constant rate stimulus has a different duration;
d) sense signals from the array of surface thoracic electrodes, and create and record therefrom surface electrocardiogram records during the repeated pacing sequences in b) and c);
e) average the surface electrocardiogram records corresponding to each of the early stimuli paced in b);
f) average the surface electrocardiogram records corresponding to each of the early stimuli paced in c); and
g) using differences between the averaged recorded surface electrocardiogram taken from e) and f), build a conduction curve that is analogous to a conduction curve obtained using endocardial measurements.

2. Apparatus according to claim 1 wherein the recording, pacing and analysis system uses a signal sensed by the at least one sensing cardiac electrode to compensate for delays and/or distortion of the surface electrocardiogram.

3. Apparatus according to claim 2 wherein the recording, pacing and analysis system uses a signal from the at least one sensing cardiac electrode to derive an interval C between the pacing stimulus provided by the pacing electrode and onset of activation of myocardium in a region proximate to the pacing electrode.

4. Apparatus according to claim 3 further comprising a clock for providing a common time reference wherein the interval derived in claim 3 for each stimulus is used to align an ECG record corresponding to that stimulus to the common time reference.

5. Apparatus according to claim 3 wherein the at least one sensing cardiac electrode and the pacing electrode are adapted to be inserted into the heart of a patient such that the distance between the pacing electrode and the at least one sensing cardiac electrode is substantially 1 cm or less.

6. Apparatus according to claim 2 further comprising a first sensing cardiac electrode of the at least one sensing cardiac electrode that is proximate to the pacing electrode and a second sensing cardiac electrode of the at least one sensing cardiac electrode that is remote to the pacing electrode.

7. Apparatus according to claim 6 wherein the system is arranged and configured to determine an interval D between a signal from the first sensing electrode resulting from the activation of myocardial tissue proximate the first electrode and a second signal from the second sensing electrode resulting from activation of myocardial tissue proximate the second electrode.

8. Apparatus according to claim 7 wherein the interval D is used by the system to time stretch or time compress individual surface electrocardiogram records so that each individual surface electrocardiogram record is the same length.

9. Apparatus according to claim 1 wherein the system is arranged and configured to introduce a pseudo-random time jitter into the constant rate stimuli.

10. Apparatus according to claim 1 wherein the system is arranged and configured to introduce a pseudo-random jitter is introduced into a first constant rate stimulus of each pacing sequence.

11. Apparatus according to claim 1 wherein the system is arranged and configured for determining the changes in duration of a response to the stimuli of the pacing sequences over the course of the pacing sequences recorded in d) and e).

12. Apparatus according to claim 11 wherein the system is arranged and configured to divide each surface electrocardiogram record into sub-records, determine a power of the potential in each sub-record and determine how the power changes in each sub-record as successive surface electrocardiogram records are added to form the averaged surface electrocardiogram record.

13. Apparatus of claim 1 wherein the system further comprises:
an amplifier coupled to the at least one sensing cardiac electrode; and
a first analog-to-digital converter coupled to the amplifier,
wherein potentials sensed by the at least one sensing cardiac electrode are amplified by the amplifier, digitized by the first analog-to-digital converter and stored in memory, and
wherein a computer program, implemented with hardware, is coupled to the pacing system and controls stimulation of the heart and recording of the potentials sensed by the at least one sensing cardiac electrode.

14. Apparatus of claim 1 further comprising:
a computer system communicatively coupled to the recording, pacing and analysis system;
a computer program;
a multichannel amplifier coupled to the array of surface thoracic electrodes;
a second analog-to-digital converter coupled to the multichannel amplifier; and
memory coupled to the second analog-to-digital converter,
wherein potentials sensed by the array of surface thoracic electrodes are amplified by the multichannel amplifier, digitized by the second analog-to-digital converter and stored in the memory, and
wherein, following a recording process, recorded data in the memory is analyzed by the computer program, executed with the computer system.

15. Apparatus of claim 1 further including a computer program, a computer system, and a memory coupled to the recording, pacing and analysis system, wherein, following a recording process, recorded data in the memory is analyzed by the computer program, executed with the computer system.

16. A method for analyzing a surface electrocardiogram (ECG) for distinguishing a physiological signal from noise, comprising:
inserting at least one sensing cardiac electrode into a heart of a patient;
inserting a pacing electrode into a heart of a patient;
placing an array of surface thoracic electrodes on a torso of the patient; and
using: a recording and pacing system coupled to the at least one sensing cardiac electrode, the pacing electrode, and the array of surface thoracic electrodes; and an analysis system, to:
a) pace the heart using the pacing electrode, in a pacing sequence comprising constant rate stimuli followed by an early stimulus, in which an interval B between the early stimulus and a preceding constant rate stimulus of the constant rate stimuli is smaller than an interval A between each stimulus of the constant rate stimuli;
b) repeat the pacing sequence multiple times wherein each time the interval B between the early stimulus and the preceding constant rate stimulus has a same duration;

c) repeat the pacing sequence multiple times wherein each time the interval B between the early stimulus and the preceding constant rate stimulus has a different duration;
d) sense signals from the array of surface thoracic electrodes, and create and record therefrom surface electrocardiogram records during the repeated pacing sequences in b) and c);
e) average the surface electrocardiogram records corresponding to each of the early stimuli paced in b);
f) average the surface electrocardiogram records corresponding to each of the early stimuli paced in c); and
g) using differences between the averaged recorded surface electrocardiogram taken from e) and f), build a conduction curve that is analogous to a conduction curve obtained using endocardial measurements.

* * * * *